(12) United States Patent
Erkmen et al.

(10) Patent No.: US 8,218,150 B2
(45) Date of Patent: Jul. 10, 2012

(54) PHASE-CONJUGATE OPTICAL COHERENCE TOMOGRAPHY METHODS AND APPARATUS

(75) Inventors: Baris I. Erkmen, Glendale, CA (US); Jeffrey H. Shapiro, Sharon, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 717 days.

(21) Appl. No.: 12/309,378

(22) PCT Filed: Jul. 17, 2007

(86) PCT No.: PCT/US2007/016162
§ 371 (c)(1),
(2), (4) Date: Jan. 15, 2009

(87) PCT Pub. No.: WO2008/091286
PCT Pub. Date: Jul. 31, 2008

(65) Prior Publication Data
US 2009/0290162 A1    Nov. 26, 2009

Related U.S. Application Data

(60) Provisional application No. 60/807,616, filed on Jul. 18, 2006, provisional application No. 60/863,529, filed on Oct. 30, 2006.

(51) Int. Cl.
*G01B 9/02* (2006.01)
(52) U.S. Cl. .................................................. 356/450
(58) Field of Classification Search .................. None
See application file for complete search history.

(56) References Cited

U.S. PATENT DOCUMENTS

| 4,979,828 | A | 12/1990 | Cronin-Golomb et al. |
| 5,120,133 | A | 6/1992 | Sica, Jr. |
| 5,229,832 | A * | 7/1993 | Gaynor ........................ 356/482 |
| 6,882,431 | B2 | 4/2005 | Teich et al. |

(Continued)

FOREIGN PATENT DOCUMENTS

DE    3700867 A1    7/1988

OTHER PUBLICATIONS

Abouraddy, A.F. et al., "Quantum-optical coherence tomography with dispersion cancellation," Phys. Rev. A 65 053817, 6 pp., 2002.

(Continued)

*Primary Examiner* — Tu Nguyen
(74) *Attorney, Agent, or Firm* — Joseph Teja, Jr.; Foley & Lardner LLP (57) ABSTRACT

Phase-conjugate optical coherence tomography (PC-OCT) methods and apparatus. PC-OCT may be employed as a three-dimensional imaging technique of interest for biomedical and other imaging applications. It shares much of the source and detection convenience of conventional OCT employing classical light sources, which is in clinical use in ophthalmology and is being developed for a variety of endoscopic optical biopsy instruments. PC-OCT offers a two-fold improvement in axial resolution and immunity to group velocity dispersion, when compared with conventional OCT, that is available from quantum optical coherence tomography (Q-OCT). PC-OCT does this without Q-OCT's need for a non-classical light source and the attendant requirement of photon-coincidence counting detection. Thus, in comparison with Q-OCT, PC-OCT is capable of producing images in measurement times similar to those of conventional OCT.

32 Claims, 6 Drawing Sheets

U.S. PATENT DOCUMENTS 7,292,342 B2 * 11/2007 Zaugg .......................... 356/451

OTHER PUBLICATIONS

De Boer, J.F. et al., "Improved signal-to-noise ratio in spectral-domain compared with time-domain optical coherence tomography," Optics Lett. 28(21), pp. 2067-2069, 2003.

Leitgeb, R. et al., "Performance of fourier domain vs. time domain optical coherence tomography," Optics Express 11(8), pp. 889-894, 2003.

Nasr, M.B. et al., Demonstration of Dispersion-Canceled Quantum-Optical Coherence Tomography, Phys. Rev. Lett. 91 (8) 083601, 4 pp., 2003.

Rollins, A.M. et al., "Optimal interferometer designs for optical coherence tomography," Optics Lett. 24(21), pp. 1484-1486, 1999.

Schmitt, J.M., "Optical Coherence Tomography (Oct): A Review," IEEE J. Sel. Top. in Quantum Electron, 5, pp. 1205-1215, 1999.

Shapiro, J.H. et al., "Semiclassical versus quantum behavior in fourth-order interference," J. Opt. Soc. Am. B 11(6), pp. 1130-1141, 1994.

Shapiro, J.H., "Quantum Gaussian Noise," Proceedings of SPIE 5111, pp. 382-395, 2003.

Sorin, W.V. et al., "A Simple Intensity Noise Reduction Technique for Optical Low-Coherence Reflectometry," IEEE Photonics Tech. Lett. 4(12), pp. 1404-1406, 1992.

Tearney, G.J., et al., "High-speed phase- and group-delay scanning with a grating-based phase control delay line," Optics Lett. 22(23) pp. 1811-1813, 1997.

Wojtkowski, M. et al., "Ultrahigh-resolution, high-speed, Fourier domain optical coherence tomography and methods for dispersion compensation," Optics Express 12(11), pp. 2404-2422, 2004.

Shapiro et al., "Imaging with Phase-Sensitive Light," *Proceedings of the International Conference Quantum Information*, Paper IthD1, Jun. 13, 2007, 2 pp.

Erkmen et al., "Phase-Conjugate Optical Coherence Tomography," *Quantum Physics*, Jul. 18, 2006, 4 pp.

Erkmen et al., "Phase-Conjugate Optical Coherence Tomography," *Physical Review A*, vol. 74, Oct. 16, 2006, 4 pp.

Erkmen et al., "Optical Coherence Tomography with Phase-Sensitive Light," *PROC. SPIE*, vol. 6305, Aug. 13, 2006, 9 pp.

E.R. Parshall and M. Cronin-Golomb, "Phase-conjugate interferometric analysis of thin films," Applied Optics 30(34): 5090-5093 (Dec. 1, 1991).

J. Le Gouet et al., "Experimental realization of phase-conjugate optical coherence tomography," Optics Letters 35(7): 1001-1003 (Apr. 1, 2010).

J. Shamir and P. Graff, "Optical Parameters of Partially Transmitting Thin Films. 1: Basic theory of a novel method for their determinations," Applied Optics 14(12): 3053-3056 (1975).

J. Shamir, "Optical parameters of partially transmitting thin films. 2: Experiment and further analysis of a novel method for their determination," Applied Optics 15(1): 120-126 (1976).

* cited by examiner

PHASE-CONJUGATE OPTICAL COHERENCE TOMOGRAPHY METHODS AND APPARATUS

GOVERNMENT SPONSORED RESEARCH

Some of the research relating to the subject matter disclosed herein was sponsored by the U.S. Army Research Office Multidisciplinary University Research Initiative, Grant No. W911NF-05-1-0197, and the United States government has certain rights to some disclosed subject matter.

BACKGROUND

Conventional Optical Coherence Tomography (OCT) is an imaging technique that has found clinical use in ophthalmology, and further is being developed for a variety of endoscopic optical biopsy instruments. Conventional OCT provides three-dimensional images of living tissue with micron-scale spatial resolution in both the transverse and axial dimensions. The transverse resolution of OCT is obtained by conventional optical scanning, while the axial resolution derives from interferometry. In particular, in conventional OCT, a broadband light source is split into signal and reference beams, which are recombined and detected (e.g., by a photodetector) after the signal beam has interacted with (i.e., been reflected from) the tissue under examination. The broadband light source used in OCT is a classical-state light beam. Accordingly, for purposes of the present disclosure, a conventional OCT imaging technique employing a classical-state light source is referred to as "classical optical coherence tomography" (C-OCT).

Figure 1:
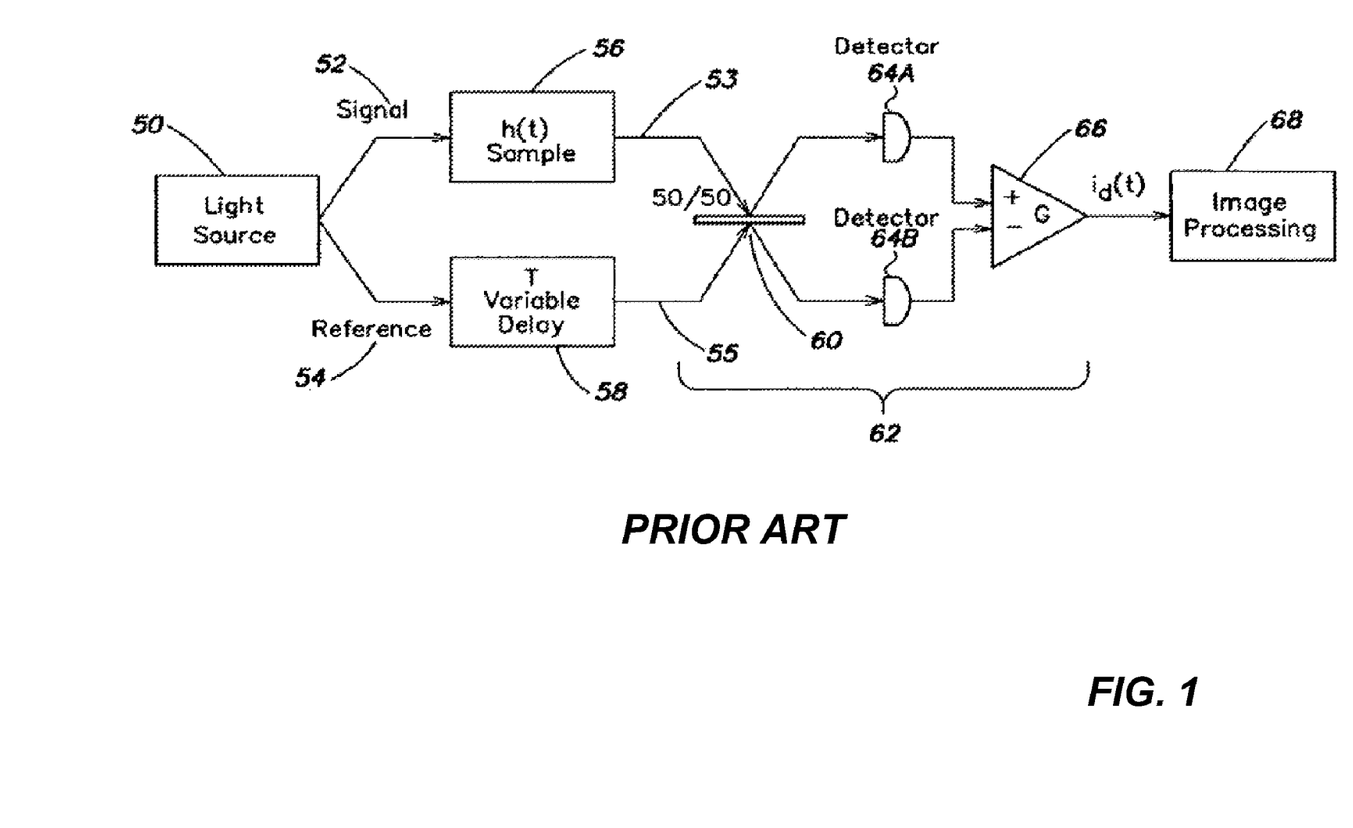
FIG. 1 generally illustrates an exemplary configuration for a classical optical coherence tomography (C-OCT) implementation.

FIG. 1 generally illustrates an exemplary configuration for a classical optical coherence tomography (C-OCT) implementation. In FIG. 1, the scanning process used to obtain transverse resolution of an imaged sample has been omitted for simplicity, as the salient concepts of interest in the present disclosure primarily are germane to axial resolution. In C-OCT, a broadband light source 50 produces classical-state light, which is divided into two beams, commonly referred to as a "signal" beam 52 and a "reference" beam 54. These signal and reference beams are in a joint classical state with a phase-insensitive correlation. Light sources 50 commonly employed for C-OCT generally have center wavelengths in the range of 590 nanometers to 1550 nanometers, bandwidths of approximately 40 to 90 nanometers, and power levels from approximately 1 mW to 100 mW. Perhaps the most common light source employed in C-OCT is a superluminescent diode (SLD). High resolution C-OCT systems use Ti:sapphire lasers with bandwidths as high as 200 nanometers at a center wavelength of approximately 800 nanometers and a power level of approximately 20 mW.

As illustrated in FIG. 1, the signal beam 52 is directed to a sample 56 to be imaged (e.g., a tissue sample) having an impulse response h(t), and the reference beam 54 is directed to a variable delay (having a delay denoted as T). The variable delay often is implemented with a moving mirror. In FIG. 1, for simplicity, the sample is shown as being irradiated by the signal beam and transmitting a beam 53 after interaction with the sample (the sample is being shown imaged in transmission), but it should be appreciated that sample imaging in C-OCT generally is done in reflection (i.e., light reflected from an irradiated sample is detected to provide the imaging information). After the signal beam has interacted with the sample and the reference beam is passed through a variable delay, the resulting beams 53 and 55 are combined in a 50/50 beam splitter 60 for detection via a measurement of second-order interference in a Michelson interferometer arrangement 62, which is followed by differential amplification in an amplifier 66 with gain G, and post-detection image processing by processor 68.

Figure 2:
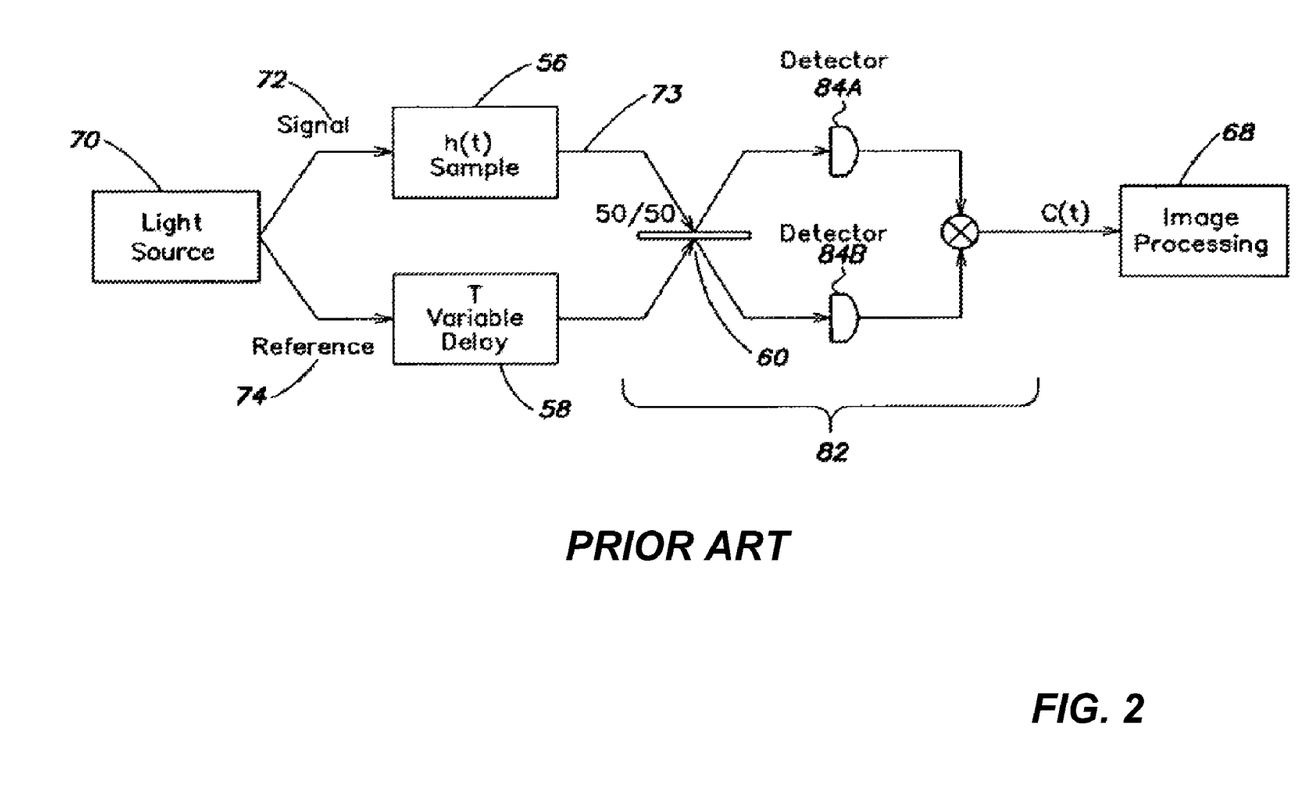
FIG. 2 generally illustrates an exemplary configuration for a quantum optical coherence tomography (Q-OCT) implementation.

Recent work with non-classical (quantum) light has led to an OCT variant known as "quantum optical coherence tomography" (Q-OCT). FIG. 2 generally illustrates an exemplary configuration for such an implementation. In FIG. 2, as in FIG. 1, the scanning process used to obtain transverse resolution of an imaged sample has been omitted for simplicity, as the salient concepts of interest in the present disclosure primarily are germane to axial resolution. Similarly, in FIG. 2, the sample 56 again is shown for simplicity as being irradiated by a signal beam 72 and transmitting a beam 73 after interaction with the sample (the sample is being shown imaged in transmission), but it should be appreciated that sample imaging in Q-OCT generally is done in reflection.

The Q-OCT implementation illustrated in FIG. 2 requires a "twin beam" non-classical light source 70, which at present is provided by the process of spontaneous parametric downconversion (SPDC). In particular, a parametric downconverter is employed to generate a signal beam 72 and a reference beam 74 having a joint-quantum state and a phase-sensitive correlation. In the low-flux limit, this non-classical Gaussian state becomes a stream of individually detectable biphotons, which is the required light source output for Q-OCT. Initial experimental demonstrations of Q-OCT employed a type-1 phase-matched lithium iodate downconverter in the light source 70, in which the generated light has a center wavelength of approximately 800 nanometers, a bandwidth of approximately 40 nanometers, and power levels between 40 picowatts and 700 picowatts. After the signal beam 72 has interacted with the sample 56 and the reference beam 74 is passed through a variable delay 58, the resulting beams are combined on a 50/50 beam splitter 60. However, the phase-sensitive signal-reference correlation cannot be measured with a Michelson interferometer; accordingly, as shown in FIG. 2, the combined beams are detected via fourth-order interference using a Hong-Ou-Mandel (HOM) interferometer arrangement 82 that is followed by post-detection image processing by the processor 68.

For the same optical source bandwidth, Q-OCT offers a two-fold improvement in axial resolution over what is obtained with C-OCT. Moreover, Q-OCT is immune to axial resolution loss caused by group velocity dispersion in propagation to and from the sample depth that is under examination (i.e., even order dispersion is cancelled). These Q-OCT advantages, however, are counterbalanced by significant disadvantages. For example, with respect to the non-classical light source employed in Q-OCT, at present the flux in the twin-beams produced by parametric downconversion typically is quite low in comparison with what is obtained from the broadband classical light sources used in C-OCT. Thus, the measurement time needed to collect a Q-OCT image is significantly longer than that for a C-OCT image. A second disadvantage of Q-OCT arises from the requirement for photon-coincidence counting detection in a Hong-Ou-Mandel interferometer, which is significantly more difficult to do than the standard Michelson interferometer measurement used in C-OCT. As a result, Q-OCT is currently a laboratory curiosity, whereas C-OCT already is employed for various clinical uses (e.g., ophthalmology, endoscopic optical biopsy instruments). Because of the low-flux nature of the twin-beams used in Q-OCT, this technique is impractical for long distance operation (e.g., laser radar). C-OCT, on the other hand, can use bright sources of light and hence may be applicable over path lengths of kilometers or longer.

SUMMARY

Notwithstanding some of the practical implementation difficulties presently associated with Q-OCT techniques, Applicants have recognized and appreciated that some of the advantages of quantum approaches to OCT, such as axial resolution improvement and immunity to group velocity dispersion, may be achieved in implementations employing high-flux (e.g., classical) light sources and standard Michelson interferometry-based detection schemes.

The inventive methods and apparatus disclosed herein are referred to generally as "phase-conjugate optical coherence tomography" (PC-OCT). PC-OCT may be employed in a manner analogous to that of conventional C-OCT techniques as a three-dimensional imaging technique (e.g., for biomedical and other applications). PC-OCT shares much of the source and detection convenience of conventional C-OCT. However, when compared with conventional C-OCT, PC-OCT offers a significant (e.g., two-fold) improvement in axial resolution and the immunity to group velocity dispersion that is available from quantum optical coherence tomography (Q-OCT). It is noteworthy that PC-OCT does this without the need for a non-classical light source employed in Q-OCT and the attendant requirement of photon-coincidence counting detection. Thus, in comparison with Q-OCT, which is still a laboratory curiosity, PC-OCT is capable of producing images in appreciably shorter measurement times (e.g., times similar to those of conventional C-OCT). Hence, it may replace conventional C-OCT in applications that demand the highest axial resolution. In addition, because PC-OCT can use bright sources, it is applicable to long-range laser radar applications and has the advantages over C-OCT of improved axial resolution and immunity to group velocity dispersion in the intervening medium.

According to one embodiment, signal and reference beams having a significant and broadband phase-sensitive correlation are employed to irradiate a sample of interest, and the phase-sensitive correlation between the beams is converted to a phase-insensitive correlation to thereby permit detection via second-order interference in a Michelson interferometer arrangement. In one aspect of this embodiment, a phase-sensitive noise may be imparted to a classical light source from which the signal and reference beams are derived, such that the signal and reference beams are in a joint classical state with a phase-sensitive correlation. In another aspect, the signal and reference beams may be in a joint quantum state with a phase-sensitive correlation.

More specifically, one inventive embodiment of the present disclosure is directed to an apparatus, comprising a light source configured to generate first radiation and second radiation having a phase-sensitive correlation, wherein the light source is configured to irradiate a sample with the first radiation, and wherein the sample, when irradiated, transmits or reflects third radiation representing a first sample interaction with the first radiation. The apparatus further comprises an optical processor configured to process the third radiation, wherein the apparatus is configured such that the sample is subsequently irradiated with the processed third radiation, and wherein the sample, when subsequently irradiated, transmits or reflects fourth radiation. The optical processor further is configured to convert the phase-sensitive correlation between the first radiation and the second radiation to a phase-insensitive correlation between the second radiation and the fourth radiation. The apparatus further comprises a Michelson interferometer configured to combine the second radiation and the fourth radiation so as to obtain information regarding the sample.

Another inventive embodiment is directed to a method, comprising acts of: A) generating first radiation and second radiation having a phase-sensitive correlation; B) irradiating a sample with the first radiation to obtain third radiation that represents a sample interaction with the first radiation; C) processing the third radiation to obtain fourth radiation, so as to convert the phase-sensitive correlation between the first radiation and the second radiation to a phase-insensitive correlation between the second radiation and the fourth radiation; and D) combining the second radiation and the fourth radiation in a Michelson interferometer so as to obtain information regarding the sample.

Another inventive embodiment is directed to an apparatus, comprising a light source configured to generate first radiation and second radiation having a phase-sensitive correlation. The light source is configured to irradiate a sample with the first radiation, wherein the sample, when irradiated, transmits or reflects third radiation representing a first sample interaction with the first radiation. The apparatus further comprises a phase-conjugator configured to receive the third radiation and generate phase-conjugated third radiation. The apparatus is configured such that the sample is subsequently irradiated with the phase-conjugated third radiation, wherein the sample, when subsequently irradiated, transmits or reflects fourth radiation representing a second sample interaction with the phase-conjugated third radiation.

Another inventive embodiment is directed to a method, comprising acts of: A) generating first radiation and second radiation having a phase-sensitive correlation; B) irradiating a sample with the first radiation to obtain third radiation that represents a first sample interaction with the first radiation; C) phase-conjugating the third radiation; and D) irradiating the sample with the phase-conjugated third radiation to obtain fourth radiation that represents a second sample interaction with the phase-conjugated third radiation.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

DETAILED DESCRIPTION

Applicants have recognized and appreciated that the factor-of-two improvement in axial resolution and the immunity to group velocity dispersion that Q-OCT affords are consequences of the how phase-sensitive noise is affected by propagation through linear media. Because high-flux classical-state light beams can carry phase-sensitive noise, it is therefore possible to reap these Q-OCT advantages without recourse to a quantum-state (e.g., "twin" beam) light source. Accordingly, one embodiment of the present disclosure is directed to imparting phase-sensitive noise to a classical light source, and utilizing the phase-sensitive noise carried by a classical light source to facilitate improved axial resolution in an OCT imaging technique. It should be appreciated, however, that in other embodiments as discussed further below, quantum light sources may be utilized to implement inventive methods and apparatus according to the present disclosure.

Figure 3:
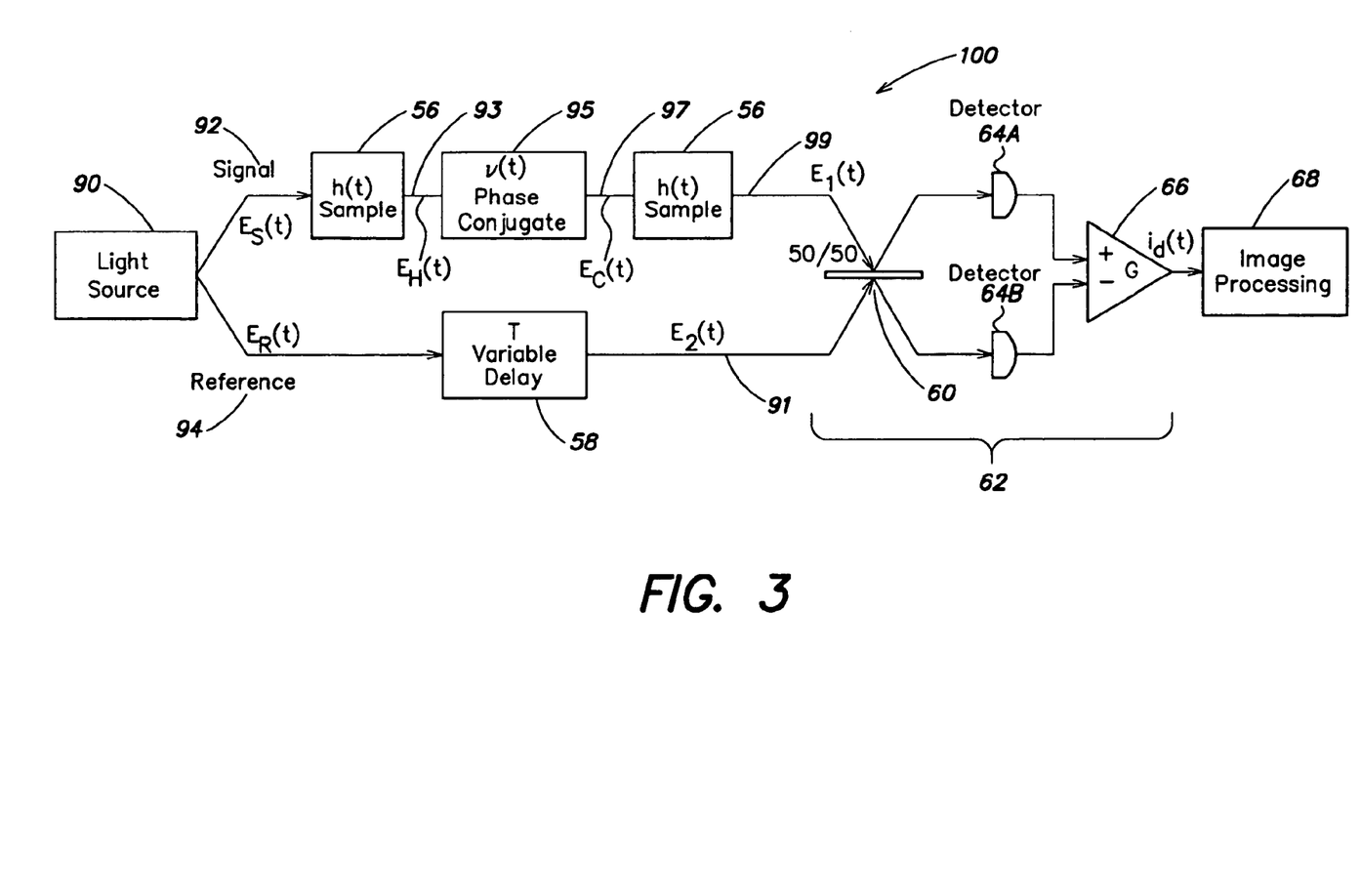
FIG. 3 generally illustrates an exemplary configuration for a phase-conjugate optical coherence tomography (PC-OCT) apparatus according to one inventive embodiment of the present disclosure.

FIG. 3 generally illustrates an exemplary configuration for a phase-conjugate optical coherence tomography (PC-OCT) apparatus 100 according to one inventive embodiment of the present disclosure. As in FIGS. 1 and 2, the scanning process used to obtain transverse resolution of an imaged sample has been omitted in FIG. 3 for simplicity, as the salient concepts of interest in the present disclosure primarily are germane to axial resolution.

In the embodiment of FIG. 3, unlike the implementations respectively shown in FIGS. 1 and 2, the light source 90 is a classical-state source that emits signal and reference beams 92 and 94 with a significant and broadband phase-sensitive signal-reference correlation (cross-correlation). Hence, the signal and reference beams 92 and 94 are said to be in a "joint classical state with a phase-sensitive correlation." In one exemplary implementation, strong signal and reference beams that have a phase-sensitive cross-correlation can be produced by splitting a single laser beam in two, and then imposing appropriate amplitude and phase noises on these beams through electro-optic modulators. Conventional optical telecommunication modulators, however, in some cases may not have sufficient bandwidth for high-resolution PC-OCT. Accordingly, in another exemplary implementation, the light source 90 exploits nonlinear optics.

For example, a light source 90 based on spontaneous parametric downconversion (SPDC) may have THz phase-matching bandwidths, and is accordingly suitable as a broadband light source for a PC-OCT implementation. Other possible light sources 90 include parametric amplification via four-wave mixing in optical fibers. In one aspect of an SPDC light source 90 for the implementation of FIG. 3, unlike Q-OCT (which relies on SPDC for the "twin beam" source, i.e., entangled biphotons), an SPDC light source for PC-OCT can (and should) be driven at maximum pump strength. In particular, it may be appreciated that there is no need to limit the photon-pair generation rate of the light source 90 so that the twin beam biphoton states are time-resolved by the approximately MHz bandwidth single-photon detectors that are used in Q-OCT's detection scheme (coincidence counter in a Hong-Ou-Mandel interferometer). To achieve maximum pump strength drive, pulsed pumping techniques may be employed. Similar techniques may be used with fiber-optic parametric amplifiers.

In FIG. 3, the signal beam 92 is directed to a sample 56 to be imaged (e.g., a tissue sample), and the reference beam 94 is directed to a variable delay. In FIG. 3, for simplicity, the sample is shown as being irradiated by the signal beam and transmitting a beam 93 after interaction with the sample (the sample is being shown imaged in transmission), but it should be appreciated that sample imaging in PC-OCT may be performed either in transmission or reflection. After the signal beam has interacted with the sample to generate the beam 93, this beam is then passed through a phase-conjugator 95. The resulting phase-conjugated beam 97 is then directed to irradiate and interact again with the sample 56 to provide a beam 99 that has twice interacted with the sample. The reference beam 94 is passed through a variable delay 58 to generate a beam 91, and the beam 91 is combined via a 50/50 beam splitter 60 with the beam 99 that has twice interacted with the sample for detection in a Michelson interferometer arrangement 62, which is followed by differential amplification by amplifier 66 with gain G, and post-detection image processing by processor 68. In sum, in one exemplary implementation according to this embodiment, the signal beam is focused on and reflected from a sample, undergoes conjugate amplification, is refocused onto the same sample, and then interfered with the time-delayed reference beam.

In one aspect of the embodiment of FIG. 3, a broadband, high-gain phase-conjugator 95 based on SPDC may be implemented as an optical parametric amplifier (OPA) used in phase-conjugation mode. For example, using a frequency-degenerate type-II phase matched down-converter as the phase-conjugator, the signal beam, after a first interaction with the sample, is applied as the beam 93 to the phase-conjugator in one input polarization (referred to as the "signal" polarization) and a vacuum state field (not shown in FIG. 3) is applied to the phase-conjugator in the other polarization (referred to as the "idler" polarization). The idler output of the phase-conjugator then serves as the beam 97, which has the characteristics needed for PC-OCT, i.e., it comprises a phase-conjugated version of the signal input plus the minimum quantum noise needed to preserve free-field commutator brackets, as discussed further below. In other exemplary implementations, similar phase-conjugate operation can also be obtained from frequency-degenerate four-wave mixing. In either of these schemes, pulsed operation may be employed to achieve a suitable gain-bandwidth product for high-performance PC-OCT.

In the embodiment of FIG. 3, because the phase conjugator 95 converts phase-sensitive correlation of the signal and reference beams to phase-insensitive correlation, the desired interference signature of the sample 56 becomes observable with the Michelson interferometer arrangement 62. However, because the signal-reference beam correlation is phase-sensitive, the configuration illustrated in the embodiment of FIG. 3 achieves the axial resolution and dispersion immunity of Q-OCT. As discussed above in connection with FIG. 2, Q-OCT derives its signal and reference beams from spontaneous parametric down-conversion (SPDC), whose outputs are in a zero-mean Gaussian state, with a non-classical phase-sensitive cross-correlation function. In the low-flux limit, this non-classical Gaussian state becomes a stream of individually detectable biphotons. Classical-state light beams can also have phase-sensitive cross-correlations, but quantum or classical phase-sensitive cross-correlations do not yield second-order interference. This is why fourth-order interference is used in Q-OCT. However, in the PC-OCT apparatus 100 of FIG. 3, the phase conjugator 95 converts a phase-sensitive cross-correlation into a phase-insensitive cross-correlation that can be seen in second-order interference.

Accordingly, it may be appreciated that it is the phase-sensitive cross-correlation of the signal and reference beams, rather than any non-classical behavior per se, that provides the axial resolution improvement and even-order dispersion cancellation. Thus, in PC-OCT, this cross-correlation need not be beyond the limits of classical physics, as is required for Q-OCT. However, as discussed further below, in other implementations a quantum light source may be utilized to generate signal and reference beams in a jointly quantum state with a phase-sensitive correlation, and a phase conjugator similarly may be employed to convert the phase-sensitive correlation to a phase-insensitive correlation.

Following below is a detailed analysis of the PC-OCT apparatus 100 shown in FIG. 3. A more rigorous theoretical analysis is provided in U.S. provisional application Ser. No. 60/807,616, filed Jul. 18, 2006, entitled "Phase-sensitive Optical Coherence Tomography Methods and Apparatus," and U.S. provisional application Ser. No. 60/863,529, filed Oct. 30, 2006, entitled "Phase-Conjugate Optical Coherence Tomography Methods and Apparatus," as well as the following publications: B. I. Erkmen and J. H. Shapiro, "Phase-conjugate optical coherence tomography," Phys. Rev. A 74, 041601 (2006); B. I. Erkmen and J. H. Shapiro, "Optical coherence tomography with phase-sensitive light," Proc. SPIE 6305, 630510 (2006); and J. H. Shapiro and B. I. Erkmen, "Imaging with Phase-Sensitive Light," in International Conference on Quantum Information Technical Digest on CD-ROM (OSA, Washington, DC, 2007), IThD1. Each of the above-identified applications and publications hereby is incorporated herein by reference.

In the apparatus 100 of FIG. 3, the signal and reference beams 92 and 94 are classical fields with a common center frequency $\omega_0$, and baseband complex envelopes, $E_S(t)$ and $E_R(t)$, with powers $\hbar\omega_0|E_K(t)|^2$, for K=S, R. These complex fields are zero-mean, stationary, jointly Gaussian random processes that are completely characterized by their phase-insensitive auto-correlations $\langle E_K^*(t+\tau)E_K(t)\rangle = F^{-1}[S(\Omega)]$, for K=S, R, and their phase-sensitive cross-correlation $\langle E_S(t+\tau)E_R(t)\rangle = F^{-1}[S(\Omega)]$, where $$F^{-1}[S(\Omega)] \equiv \int_{-\infty}^{\infty} \frac{d\Omega}{2\pi} S(\Omega) e^{-i\Omega\tau}, \quad (1)$$

is the inverse Fourier transform of $S(\Omega)$, and $S(\Omega)=S(-\Omega)\geq 0$ is the common spectrum of the signal and reference beams at detunings $\pm\Omega$ from $\omega_0$. These fields have the maximum phase-sensitive cross-correlation that is consistent with classical physics.

The signal beam is focused on a transverse spot on the sample yielding a reflection with complex envelope $E_H(t)=E_S(t)$ å $h(t)$, where å denotes convolution and $h(t)=F^{-1}[H(\Omega)]$ with $$H(\Omega) = \int_0^\infty dz\, r(z, \Omega) e^{i2\phi(z,\Omega)} \quad (2)$$

being the sample's baseband impulse response. In Eq. (2), $r(z, \Omega)$ is the complex reflection coefficient at depth z and detuning $\Omega$, and $\phi(z,\Omega)$ is the phase acquired through propagation to depth z in the sample. After conjugate amplification, the complex envelope $E_C(t)=[E_H^*(t)+w(t)]$å$v(t)$ is obtained, where w(t), a zero-mean, complex-valued, isotropic white Gaussian noise with correlation function $\langle w^*(t+\tau)w(t)\rangle=\delta(\tau)$, is the quantum noise injected by the conjugation process, and $v(t)=F^{-1}[V(\Omega)]$ gives the conjugator's baseband impulse response in terms of its frequency response. The output of the conjugator is refocused onto the sample resulting in the positive-frequency field $E_1(t)=[E_C(t)$ å $h(t)]e^{-i\omega_0 t}$, which is interfered with $E_2(t)=E_R(t-T)e^{-i\omega_0(t-T)}$ in a Michelson interferometer, as shown in FIG. 3. The photodetectors 64A and 64B in FIG. 3 are assumed to have quantum efficiency η, no dark current, and thermal noise with a white current spectral density $S_{i_{th}}$. The average amplified difference current, which constitutes the PC-OCT signature, is then $$\langle i_d(t)\rangle = 2q\eta G_A \text{Re}\left(\int_{-\infty}^{\infty} \frac{d\Omega}{2\pi} H^*(-\Omega)H(\Omega) \times V^*(-\Omega)S(\Omega)e^{-i(\Omega-\omega_0)T}\right), \quad (3)$$

where q is the electron charge and $G_A$ is the amplifier gain.

In C-OCT the signal and reference inputs have complex envelopes that are zero-mean, stationary, jointly Gaussian random processes which are completely characterized by their phase-insensitive auto- and cross-correlations, $\langle E_J^*(t+\tau)E_K(t)\rangle=F^{-1}[S(\Omega)]$, for J, K=S, R. As shown in FIG. 1, in C-OCT the sample is illuminated with the signal beam and the reflected signal—still given by convolution of $E_S(t)$ with h(t)—is interfered with the delayed reference beam in a Michelson interferometer. Thus, the average amplified difference current in C-OCT is $$\langle i_d(t)\rangle = 2q\eta G_A$$

$$\times \text{Re}\left(\int_{-\infty}^{\infty} \frac{d\Omega}{2\pi} H^*(-\Omega)S(\Omega)e^{-i(\Omega-\omega_0)T}\right). \quad (4)$$

For Q-OCT, quantum fields must be used because non-classical light is involved. Now the baseband signal and reference beams are photon-units field operators, $\hat{E}_S(t)$ and $\hat{E}_R(t)$, with the following non-zero commutators, $[\hat{E}_J(t), \hat{E}_K^\dagger(u)]=\delta_{JK}\delta(t-u)$, for J, K=S, R. In Q-OCT, the sample is illuminated with $\hat{E}_S(t)$ and then the field operator is applied for the reflected beam plus that for the reference beam to an HOM interferometer, as shown in FIG. 2. The familiar biphoton HOM dip can be obtained theoretically—in a manner that is the natural quantum generalization of the classical Gaussian-state analysis employed herein—by taking the signal and reference beams to be in a zero-mean joint Gaussian state that is completely characterized by the phase-insensitive (normally-ordered) auto-correlations $\langle \hat{E}_K^\dagger(t+\tau)\hat{E}_K(t)\rangle=F^{-1}[S(\Omega)]$, for K=S, R, and the phase-sensitive cross-correlation $\langle \hat{E}_S(t+\tau)\hat{E}_R(t)\rangle=F^{-1}[\sqrt{S(\Omega)(S(\Omega)+1)}]$. This joint signal-reference state has the maximum possible phase-sensitive cross-correlation permitted by quantum mechanics. In the usual biphoton limit wherein HOM interferometry is performed, $S(\Omega)\square 1$ prevails, and the average photon-coincidence counting signature can be shown to be $$\langle C(T)\rangle = \quad (5)$$

$$\frac{q^2\eta^2}{2}\left[\int_{-\infty}^{\infty} \frac{d\Omega}{2\pi}|H(\Omega)|^2 S(\Omega) - \text{Re}\left(\int_{-\infty}^{\infty} \frac{d\Omega}{2\pi} H^*(-\Omega)H(\Omega)S(\Omega)e^{i2\Omega T}\right)\right].$$

Figure 4A:
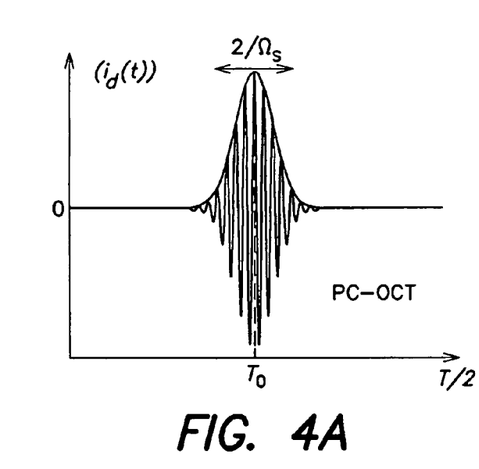
FIGS. 4A, 4B and 4C illustrate exemplary output signal profiles for PC-OCT, C-OCT and Q-OCT, respectively.
Figure 4B:
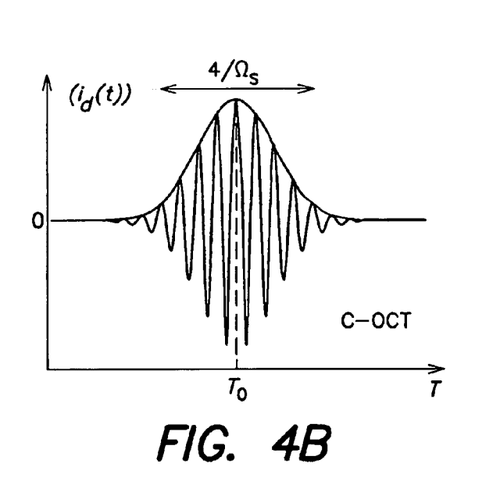
Figure 4C:
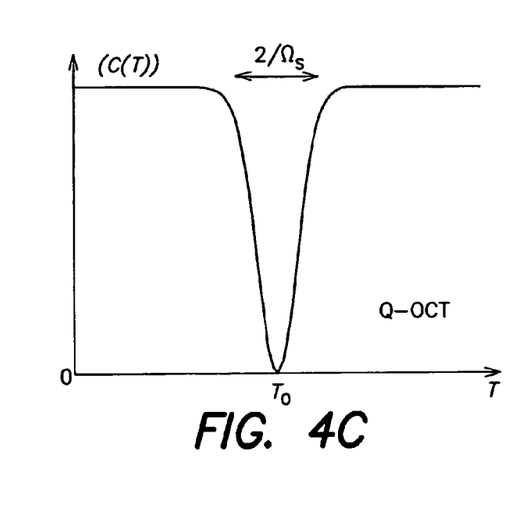

For purpose of the present analysis, it is assumed that $$V^*(-\Omega)S(\Omega) \approx V^*S(\Omega) = (V^*P_S\sqrt{2\pi/\Omega_S^2})e^{-\Omega^2/2\Omega_S^2}$$

and $$H(\Omega) = re^{i(\omega_0 + \Omega)T_0},$$

with $|r| \ll 1$. Physically, this corresponds to having a conjugate amplifier whose bandwidth is much broader than that of the signal-reference source, and a sample that is a weakly-reflecting mirror at delay $T_0$. Eq. (3) then gives a PC-OCT average amplified difference current that, as a function of the reference-arm delay T, is a sinusoidal fringe pattern of frequency $\omega_0$ with a Gaussian envelope proportional to $e^{-2\Omega_S^2(T_0-T/2)^2}$, as illustrated in FIG. 4A. The average amplified difference current in C-OCT behaves similarly: from Eq. (4), it may be observed that it too is a sinusoidal, frequency $\omega_0$ fringe pattern in T, but its envelope is proportional to $e^{-\Omega_S^2(T_0-T)^2/2}$, as shown in FIG. 4B. The signature of Q-OCT, found from Eq. (5), is a dip in the average coincidence-count versus reference-arm delay that is proportional to $e^{-2\Omega_S^2(T_0-T)^2}$, as shown in FIG. 4C. Defining the axial resolutions of these OCT systems to be the full-width between the $e^{-2}$ attenuation points in their Gaussian envelopes viewed as functions of $T_0$ shows that PC-OCT and Q-OCT both achieve factor-of-two improvements over C-OCT for the same source bandwidth.

To probe the effect of dispersion on PC-OCT, C-OCT, and Q-OCT, the sample's frequency response is modified to $H(\Omega) = re^{i[(\omega_0+\Omega)T_0 + b\Omega^2/2]}$, where b is a non-zero real constant representing second-order (group-velocity) dispersion. Because the sample's frequency response enters the PC-OCT and Q-OCT signatures as $H^*(-\Omega)H(\Omega)$, neither one is affected by this dispersion term in $H(\Omega)$, i.e., it cancels out. For C-OCT, however, it may be observed that the Gaussian envelope of the average amplified difference current is now proportional to $e^{-\Omega_S^2(T_0-T)^2/2(1+\Omega_S^4 b^2)}$, i.e., its axial resolution becomes badly degraded when $\Omega_S^4 b^2 \gg 1$. More generally, for $H(\Omega) = re^{i[(\omega_0+\Omega)T_0 + \beta(\Omega)]}$, PC-OCT and Q-OCT are immune to dispersion created by the even-order terms in the Taylor series expansion of $\beta(\Omega)$.

Having shown that PC-OCT retains the key advantages of Q-OCT, the SNR behavior of PC-OCT is examined. Because Q-OCT relies on SPDC to generate the entangled biphoton state, and Geiger-mode avalanche photodiodes 84A and 84B (see FIG. 2) to perform photon-coincidence counting, its image acquisition is much slower than that of C-OCT, which can use bright sources and linear-mode detectors. To assess the SNR of PC-OCT, a Gaussian spectrum is used for $S(\Omega)$ and the non-dispersing mirror for $H(\Omega)$, but, in order to limit its quantum noise, the conjugator's frequency response is taken to be $V(\Omega) = Ve^{-\Omega^2/4\Omega_V^2}$. It is assumed that $i_d(t)$ is time averaged for $T_I$ seconds (denoted $\langle i_d(t) \rangle_{T_I}$) at the reference-arm delay that maximizes the interference signature, and the following parameter is defined:

$$SNR_{PC-OCT} = \langle i_d(t)\rangle^2 / \text{var}[\langle i_d(t)\rangle_{T_I}].$$

When the w(t) contribution to the conjugator's output dominates the $E_H(t)$ contribution, it is found that $$SNR_{PC-OCT} = \frac{8T_I\eta|r|^4|V|^2 P_S^2 \Omega_V^2/(\Omega_S^2 + 2\Omega_V^2)}{\left[\Omega_{th} + P_S + |rV|^2\sqrt{\Omega_V^2/2\pi} + \frac{2\eta|rV|^2 P_S\Omega_V}{\sqrt{\Omega_S^2 + \Omega_V^2}}\right]}, \quad (6)$$

where $\Omega_{th} \equiv S_{i_{th}}/q^2\eta$. From left to right the terms in the noise denominator are the thermal noise, the reference-arm shot noise, the conjugate-amplifier quantum noise, and the intrinsic noise of the signal×reference interference pattern itself. Best performance is achieved when the conjugator gain $|V|^2$ is large enough to neglect the first two noise terms, and the input power $P_S$ is large enough that the intrinsic noise greatly exceeds the conjugator's quantum noise. In this case, it is observed that $$SNR_{PC-OCT} = \frac{4T_I|r|^2 P_S \Omega_V \sqrt{\Omega_S^2 + \Omega_V^2}}{\Omega_S^2 + 2\Omega_V^2}. \quad (7)$$

To compare the preceding SNR to that for C-OCT, the parameter $$SNR_{C-OCT} = \langle i_d(t)\rangle^2 / \text{var}[\langle i_d(t)\rangle^2]$$

is defined for the FIG. 1 configuration at the peak of the C-OCT interference signature. When the reflected signal field is much weaker than the reference field, it is observed that $$SNR_{C-OCT} = 4\eta T_I |r|^2 P_S, \quad (8)$$

which can be smaller than the ultimate $SNR_{PC-OCT}$ result. However, if PC-OCT's conjugator gain is too low to reach this ultimate performance, but its reference-arm shot noise dominates the other noise terms, it is observed that $$SNR_{PC-OCT} = \frac{8\eta T_I|r|^4|V|^2 P_S \Omega_V^2}{\Omega_S^2 + 2\Omega_V^2}, \quad (9)$$

which is substantially lower than $SNR_{C-OCT}$, because $|rV|^2 \ll 1$ is implicit in the assumption that the reference shot noise is dominant as high detector quantum efficiency can be expected. Thus, PC-OCT has SNR similar to that of C-OCT, but only if high-gain phase conjugation is available.

At this juncture it is worth emphasizing the fundamental physical point revealed by the preceding analysis. The use of entangled biphotons and fourth-order interference measurement in an HOM interferometer enable Q-OCT's two performance advantages over C-OCT: a factor-of-two improvement in axial resolution and cancellation of even-order dispersion. Classical phase-sensitive light also produces an HOM dip with even-order dispersion cancellation, but this dip is essentially unobservable because it rides on a much stronger background term. Thus, the non-classical character of the entangled biphoton is the source of Q-OCT's benefits, from which it might be concluded that non-classical light is required for any OCT configuration with these performance advantages over C-OCT. Such is not the case, however, because the PC-OCT configuration described herein illustrates that it is really phase-sensitive cross-correlations that are at the root of axial resolution enhancement and even-order dispersion cancellation. Phase-sensitive cross-correlations cannot be seen in the second-order interference measurements used in C-OCT. PC-OCT therefore phase conjugates one of the phase-sensitive cross-correlated beams, converting their phase-sensitive cross-correlation into a phase-insensitive cross-correlation that can be seen in second-order interference.

The analysis herein of PC-OCT assumed classical-state light, and because $S(0) \ll 1$ is required for high-SNR PC-OCT operation, little further can be expected in the way of performance improvement by using non-classical light in PC-OCT. This can be seen by comparing the cross-spectra $S(\Omega)$ and $\sqrt{S(\Omega)(S(\Omega)+1)}$ when $$S(\Omega) = (P_S\sqrt{2\pi/\Omega_S^2})e^{-\Omega^2/2\Omega_S^2},$$

with $P_S\sqrt{2\pi/\Omega_S^2} \Box 1$. The intimate physical relation between PC-OCT and Q-OCT can be further elucidated by considering the way in which the sample's frequency response enters their measurement averages. Again it is assumed that $V^*(-\Omega)S(\Omega) \approx V^*S(\Omega)$, so that both imagers yield signatures $\propto \int d\Omega H^*(-\Omega)H(\Omega)S(\Omega)$. Klyshko's advanced-wave interpretation has been used to account for the $H^*(-\Omega)H(\Omega)$ factor in the Q-OCT signature as the product of an actual sample illumination and a virtual sample illumination. In the PC-OCT apparatus disclosed herein, this same $H^*(-\Omega)H(\Omega)$ factor comes from the two sample illuminations, one before phase conjugation and one after. In both cases, it is the phase-sensitive cross-correlation that is responsible for this factor. Q-OCT uses non-classical light and fourth-order interference while PC-OCT can use classical light and second-order interference to obtain the same sample information.

That PC-OCT's two sample illuminations provide an axial resolution advantage over C-OCT leads naturally to considering whether C-OCT would also benefit from two sample illuminations. To this end, consider the general arrangement of the PC-OCT apparatus 100 shown in FIG. 3, with $E_S(t)$ and $E_R(t)$ instead arising from a C-OCT light source 50 as shown in FIG. 1, and the phase-conjugate amplifier (phase conjugator) 95 replaced with a conventional phase-insensitive amplifier of field gain $G(\Omega) = Ge^{-\Omega^2/4\Omega_G^2}$ with $|G|\Box 1$. Such a two-pass C-OCT arrangement then yields an interference signature $\propto e^{-2\Omega_S^2(T_0-T/2)^2}$ for the weakly-reflecting mirror when the amplifier is sufficiently broadband, and an SNR given by Eq. (6) with V replaced by G and $\Omega_V$ replaced by $\Omega_G$. Thus, two-pass C-OCT has the same axial resolution advantage and SNR behavior as PC-OCT. However, instead of providing even-order dispersion cancellation, two-pass C-OCT doubles all the even-order dispersion coefficients.

In summary, the foregoing analysis demonstrates that the PC-OCT apparatus 100 shown in the embodiment of FIG. 3 combines many of the best features of conventional OCT and quantum OCT. Like C-OCT, PC-OCT relies on second-order interference in a Michelson interferometer. Thus it can use linear-mode avalanche photodiodes (APDs), rather than the lower bandwidth and less efficient Geiger-mode APDs employed in Q-OCT. Like Q-OCT, PC-OCT enjoys a factor-of-two axial resolution advantage over C-OCT, and automatic cancellation of even-order dispersion terms. The source of these advantages, for both Q-OCT and PC-OCT, is the phase-sensitive cross-correlation between the signal and reference beams. In PC-OCT, however, this cross-correlation need not be beyond the limits of classical physics, as is required for Q-OCT. Finally, PC-OCT may achieve an SNR comparable to that of C-OCT, thus realizing much faster image acquisition than is currently possible in Q-OCT.

It should be appreciated that while an exemplary sample including a biological tissue is illustrated in FIG. 3, PC-OCT techniques according to the present disclosure may be employed essentially in any imaging application requiring micron-scale imaging over relatively short working distances. Other exemplary applications in addition to tissue imaging include, but are not limited to, nondestructive inspection for micro cracks in manufactured parts (e.g., on an assembly line), nondestructive evaluation of highly scattering polymer-matrix composites to estimate residual porosity, fiber architecture and structural integrity, and nondestructive evaluation of paints and coatings. PC-OCT also may be applied to long range (>1 kilometer) imaging scenarios in which its dual benefits of improved axial resolution and immunity to group velocity are advantageous.

According to yet another embodiment, instead of employing classical-state signal and reference beams with a phase-sensitive correlation as discussed above in connection with FIG. 3, quantum-state signal and reference beams with a phase-sensitive correlation alternatively may be employed as a light source (e.g., as discussed above in connection with the Q-OCT technique illustrated in FIG. 2). However, unlike the Q-OCT implementation, the signal beam of the jointly quantum-state beams in this alternative embodiment still is phase-conjugated (i.e., passed through a phase-conjugator), thereby permitting the use of the simpler Michelson interferometer for the detection scheme (rather than the photon-coincidence counting Hong-Ou-Mandel interferometer required in FIG. 2). In this manner, source fluxes for the quantum-state source that are beyond the counting limit of available single-photon counters may be used (e.g., source fluxes in the milliwatt range), as linear-mode avalanche photodiode detectors may be employed in the Michelson interferometer detection arrangement.

Figure 5:
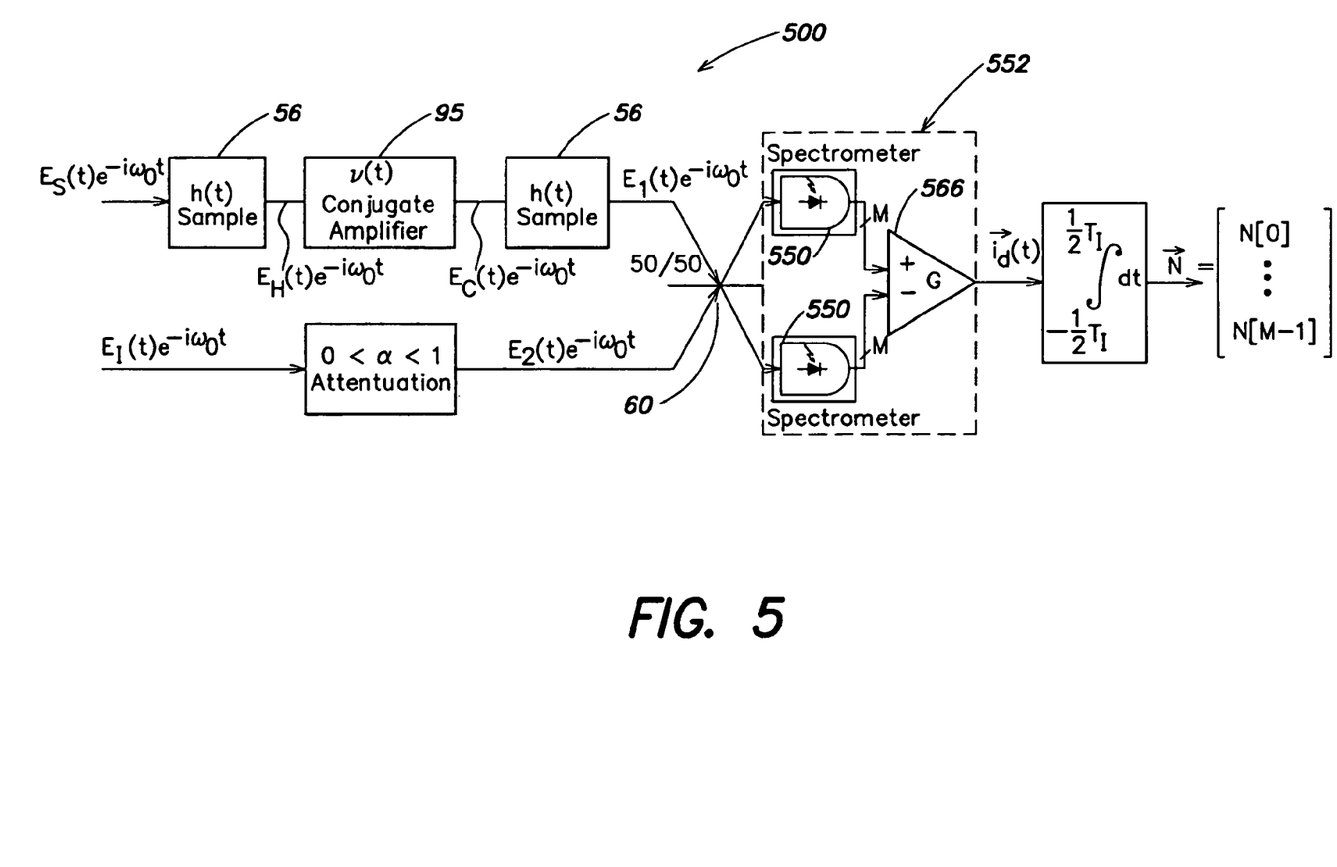
FIG. 5 illustrates an exemplary configuration for a frequency domain PC-OCT apparatus, according to one inventive embodiment of the present disclosure.

FIG. 5 illustrates an exemplary configuration for a frequency domain PC-OCT apparatus 500, according to one inventive embodiment of the present disclosure. The block diagram shown in FIG. 5 is substantially similar to that shown in FIG. 3 for the time domain, except for the absence of the variable delay 58 (T) and the replacement of the detectors 64A and 64B in the Michelson interferometer arrangement with two identical spectrometers 550. In one aspect of this embodiment, the apparatus 500 estimates the second-order interference spectrum, which may be inverse Discrete Fourier transformed to obtain an interference fringe very similar to that obtained in the time-domain. In another aspect, the resolution of the spectrometers and the bandwidth of the source determine the measurement resolution of the apparatus. In yet another aspect, the apparatus 500 has no moving components, which in some instances may increase stability when imaging at kHz rates.

Figure 6:
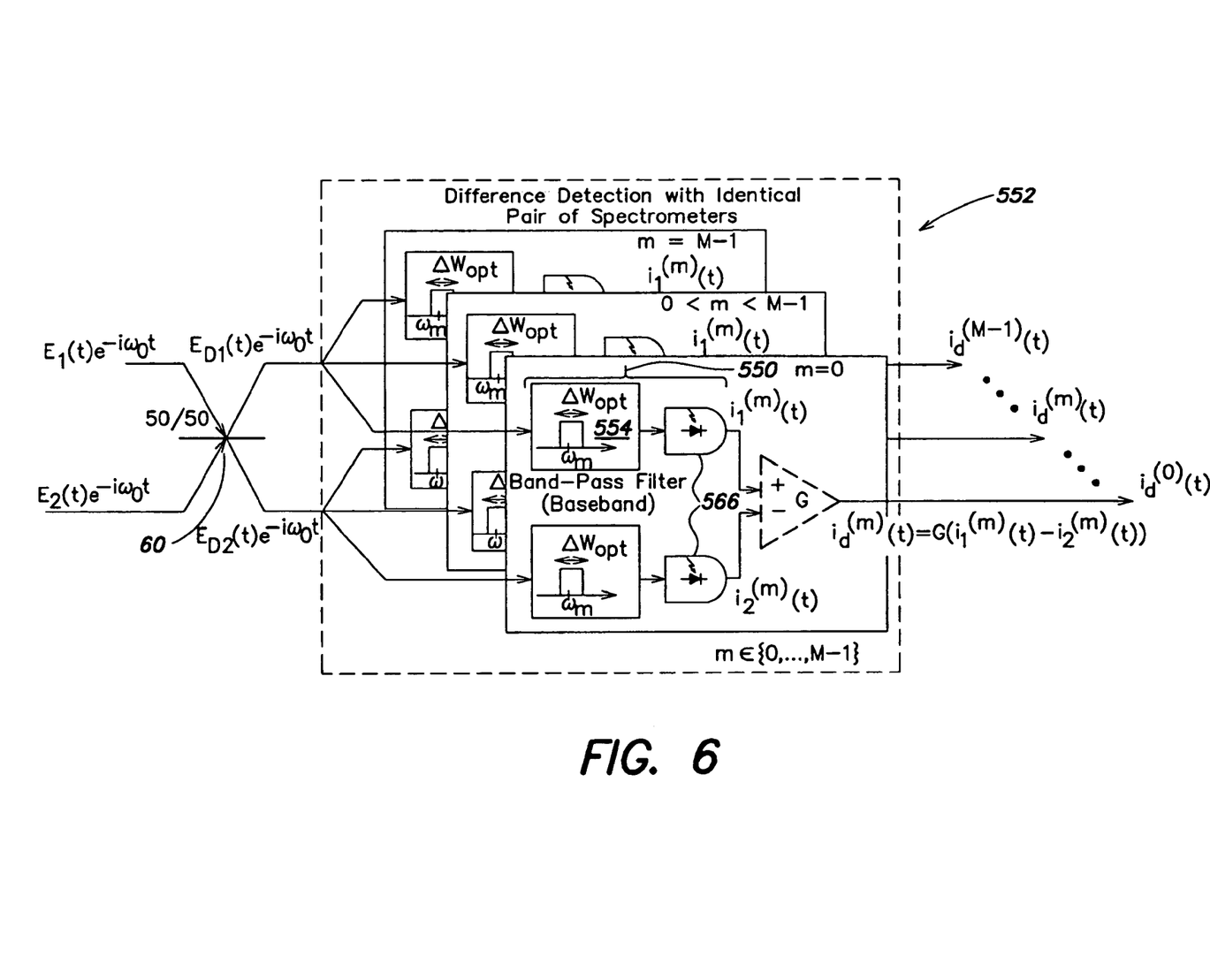
FIG. 6 illustrates an analytical model of a spectrometer of the frequency domain PC-OCT apparatus shown in FIG. 5.

FIG. 6 illustrates an analytical model of the spectrometers 550 of the frequency domain PC-OCT apparatus shown in FIG. 5. As shown in FIG. 6, each spectrometer 550 is modeled as comprising M parallel detectors 566, each detector preceded by a narrowband optical filter 554 tuned to different center frequencies, such that the M detectors collectively cover non-overlapping, adjacent frequency bands over the optical bandwidth of the spectrometer. In one aspect, the baseband equivalent center frequencies of the M detectors are designated as $\omega_m$ (i.e., the carrier frequency of the incoming light, $\omega_0$, is subtracted out) and the optical bandwidth of the $m^{th}$ detector is $\Delta W_{opt} \Box 1$. The outputs of a given spectrometer are the M current values obtained from the detectors. The currents from the two spectrometers are subtracted to obtain $\vec{i}(t) = i_d^{(m)}(t) | m = 0, \ldots, M-1\}$, a M×1 vector of difference currents. Similar to time-domain PC-OCT, each difference current is integrated over a period $T_I$ to obtain an estimate of the spectrum as follows:

$$N[m] = \frac{1}{T_I} \int_{-(\frac{1}{2})T_I}^{(\frac{1}{2})T_I} i_d^{(m)}(t)dt,$$

where $m = 0, \ldots, M-1$. The inverse Discrete Fourier Transform (DFT) of the estimate waveform is taken to obtain a signature that resembles the signature of time-domain OCT system.

Note that this frequency-domain technique has some relevant distinctions from time-domain PC-OCT techniques. First, in frequency-domain PC-OCT, the acquisition of data occurs in parallel, rather than serial data acquisition in time-domain PC-OCT. However, because the optical bandwidth of the light illuminating each detector is appreciably smaller in frequency-domain OCT, the integration time must also be longer. Because integration times are on the order of the inverse of the optical bandwidth of the illuminating field, the data acquisition times of time-domain and frequency-domain techniques are almost the same. However, frequency-domain techniques have the advantage of eliminating the time-varying delay in the reference branch, which improves stability of the interference by eliminating jitter from mechanical motion (time-varying delay is often implemented with a moving mirror).

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A method, comprising acts of:
  A) generating first radiation and second radiation having a broadband phase-sensitive correlation;
  B) irradiating a sample with the first radiation to obtain third radiation that represents a first sample interaction with the first radiation;
  C) phase-conjugating the third radiation; and
  D) irradiating the sample with the phase-conjugated third radiation to obtain fourth radiation that represents a second sample interaction with the phase-conjugated third radiation.

2. The method of claim 1, wherein the first radiation and the second radiation have a joint classical state.

3. The method of claim 2, wherein the act A) comprises:
A1) generating the first radiation and second radiation as first and second classical-state light beams having phase-sensitive noise.

4. The method of claim 3, wherein the act A1) comprises: amplitude modulating the first and second classical-state light beams to provide the phase-sensitive noise.

5. The method of claim 3, wherein the act A1) comprises: phase modulating the first and second classical-state light beams to provide the phase-sensitive noise.

6. The method of claim 1, wherein the first radiation and the second radiation have a joint quantum state.

7. The method of claim 6, wherein the act A) comprises: generating the first radiation and second radiation as first and second beams via four-wave mixing.

8. The method of claim 6, wherein the act A) comprises: generating the first radiation and second radiation as first and second beams via parametric downconversion.

9. The method of claim 1, wherein the sample includes a biological tissue.

10. The method of claim 1, wherein the sample is a manufactured part.

11. The method of claim 1, wherein the sample includes a paint or other coating for a surface.

12. The method of claim 1, wherein the act C) comprises: passing the third radiation through a four-wave mixer so as to obtain the phase-conjugated third radiation.

13. The method of claim 1, wherein the act C) comprises: passing the third radiation through an optical parametric amplifier so as to obtain the phase-conjugated third radiation.

14. The method of claim 1, further comprising acts of:
E) combining the second radiation and the fourth radiation to provide combined radiation; and
F) processing the combined radiation to obtain information regarding the sample.

15. The method of claim 14, further comprising an act of variably delaying the second radiation prior to the act E).

16. The method of claim 14, wherein the act E) comprises an act of:
passing the second radiation and the fourth radiation through a beam splitter.

17. The method of claim 14, wherein the act F) comprises an act of:
processing the combined radiation to obtain an image of at least a portion of the sample.

18. An apparatus, comprising:
a light source configured to generate first radiation and second radiation having a broadband phase-sensitive correlation, the light source configured to irradiate a sample with the first radiation, wherein the sample, when irradiated, transmits or reflects third radiation representing a first sample interaction with the first radiation; and
a phase-conjugator configured to receive the third radiation and generate phase-conjugated third radiation, wherein the apparatus is configured such that the sample is subsequently irradiated with the phase-conjugated third radiation, and wherein the sample, when subsequently irradiated, transmits or reflects fourth radiation representing a second sample interaction with the phase-conjugated third radiation.

19. The apparatus of claim 18, wherein the light source is configured such that the first radiation and the second radiation have a joint classical state.

20. The apparatus of claim 19, wherein the light source is configured so as to generate the first radiation and second radiation as first and second classical-state light beams having phase-sensitive noise.

21. The apparatus of claim 20, further comprising at least one amplitude modulator configured to modulate an amplitude of the first and second classical-state light beams to provide the phase-sensitive noise.

22. The apparatus of claim 20, further comprising at least one phase modulator configured to modulate a phase of the first and second classical-state light beams to provide the phase-sensitive noise.

23. The apparatus of claim 18, wherein the light source is configured such that the first radiation and the second radiation have a joint quantum state.

24. The apparatus of claim 23, wherein the light source includes a parametric downconverter configured to generate the first radiation and second radiation as first and second beams.

25. The apparatus of claim 23, wherein the light source includes a four-wave mixer configured to generate the first radiation and second radiation as first and second beams.

26. The apparatus of claim 18, further comprising the sample, wherein the sample includes a biological tissue.

27. The apparatus of claim 18, further comprising the sample, wherein the sample is a manufactured part.

28. The apparatus of claim 18, wherein the phase-conjugator includes an optical parametric amplifier.

29. The apparatus of claim 18, wherein the phase-conjugator includes a four-wave mixer.

30. The apparatus of claim 18, further comprising:
a 50/50 beam splitter configured to combine the second radiation and the fourth radiation to provide combined radiation; and
at least one processor configured to process the combined radiation to obtain information regarding the sample.

31. The apparatus of claim 30, further comprising:
a variable delay disposed in an optical path between the light source and the 50/50 beam splitter and configured to variably delay the second radiation prior to combining the second radiation and the fourth radiation.

32. The apparatus of claim 30, wherein the at least one processor is configured to process the combined radiation to obtain an image of at least a portion of the sample.

* * * * *